US00PP25803P2

(12) United States Plant Patent
Osiecki

(10) Patent No.: US PP25,803 P2
(45) Date of Patent: Aug. 11, 2015

(54) ***ALOCASIA* PLANT NAMED 'ALO3'**

(50) Latin Name: ***Alocasia* hybrid**
Varietal Denomination: ALO3

(71) Applicant: Marian Osiecki, Marianna, FL (US)

(72) Inventor: Marian Osiecki, Marianna, FL (US)

(73) Assignee: Ogrsby Plants International, Inc., Altha, FL (US)

( * ) Notice: Subject to any disclaimer, the term of this patent is extended or adjusted under 35 U.S.C. 154(b) by 159 days.

(21) Appl. No.: 13/986,615

(22) Filed: May 16, 2013

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Cassandra Bright

(57) ABSTRACT

A new and distinct *Alocasia* cultivar named 'ALO3' is disclosed, characterized by medium size, dark green, thick glossy foliage, very vigorous growth with very early and abundant basal shoot production. The new variety has closely overlapping, sagittate to nearly hastate leaf blades with narrow silver shadowing and glossy dark burgundy under leaf, as well as contrasting light pink petioles with green or brown streaks. The new variety is very easy to grow under low or high light conditions and well as low or high temperature conditions and is suitable for 6-8 inch pot production from a single tissue culture plantlet. The new variety is an *Alocasia*, typically produced as an ornamental plant.

1 Drawing Sheet

Latin name of the genus and species: *Alocasia* hybrid.
Variety denomination: 'ALO3'.

BACKGROUND OF THE INVENTION

The new cultivar is a product of a planned breeding program. The objectives of the planned breeding program were to develop new *Alocasia* varieties of small to medium size, with fast growth, strong basal shoot production, long shelf life, suitable for 6-8 inch commercial pot production. Additional feature sought were thick leaves and colorful, strongly contrasting leaf peduncles. The new variety originated from a cross pollination of an unpatented seed parent referred to as 'Aurora' and the pollen parent, the unpatented variety of *Alocasia* known as 'Polly'. The crossing was made during May of 2007.

The new variety was discovered by the inventor, Marian Osiecki, a citizen of the US, in October of 2008 in a group of seedlings resulting from the crossing. The new cultivar was found in a commercial greenhouse in Altha, Fla.

Asexual reproduction of the new cultivar 'ALO3' was first performed at a commercial laboratory in Altha, Fla. by tissue culture on Jan. 29, 2009. Subsequent propagation by tissue culture has shown that the unique features of this cultivar are stable and reproduced true to type.

SUMMARY OF THE INVENTION

The cultivar 'ALO3' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALO3'. These characteristics in combination distinguish 'ALO3' as a new and distinct *Alocasia* cultivar:

1. Medium size plants with very fast, vigorous growth and strong basal shoot production.
2. Very symmetrical growth habit.
3. Dark green, thick, glossy foliage with veins surrounded by a narrow silver shadow.
4. Dark burgundy and glossy lower side of the leaf blade.
5. Closely overlapping, sagittate to hastate leaf blades.
6. Very strong, thick, light pink petioles with green or brown streaks.
7. Very easy to grow even under low or high light conditions
8. Very easy to grow in low or high temperatures.
9. Exceptionally long 6-8 months shelf life.
10. 'ALO3' is suitable for production in 6-8" pots from a single tissue culture plantlet.
11. Strong plant, tolerant of stressful conditions.

PARENT COMPARISON

Plants of the new cultivar 'ALO3' are similar to the unpatented seed parent 'Aurora' in most horticultural characteristics. The new variety however differs in the following characteristics:

1. 'ALO3' is a more vigorous and faster growing plant than 'Aurora'.
2. ALO3' is a shorter plant, in a 6" pot it is 30-35 cm tall compared to 'Aurora, 50-60 cm tall.
3. Plants of 'ALO3' are more symmetrical and narrower in diameter compared to 'Aurora'.
4. Plants of 'ALO3' are denser and less open in form compared to 'Aurora'.
5. The leaf blades of 'ALO3' are smaller, darker green, thicker and glossier compared to leaf blades of 'Aurora'.
6. Leaf veins of 'ALO3' are thicker, having a darker and broader silver shadow than 'Aurora'.

7. The lower side of 'ALO3' leaf blade is burgundy and glossy whereas the lower side of 'Aurora' leaf blade is green and matte.
8. Leaf blades of 'ALO3' are oriented horizontally whereas the leaf blades of 'Aurora' are oriented downward.
9. Leaf petioles of 'ALO3' are thicker and much stronger than petioles of 'Aurora'.
10. Leaf petioles of 'ALO3' are light pink with delicate green streaks whereas the leaf petioles of 'Aurora' are darker pink with less distinctive green streaks.
11. 'ALO3' is a stronger plant, with a longer shelf life, and more tolerant of disease and stress conditions than 'Aurora'.

Plants of the new cultivar 'ALO3' are similar to the pollen parent, the unpatented, variety of *Alocasia* know as 'Polly' in most horticultural characteristics. The new variety however differs in the following characteristics:

1. 'ALO3' is a more vigorous, taller and faster growing plant than 'Polly'.
2. 'ALO3' produces basal shoots earlier and more abundantly than 'Polly'.
3. 'ALO3' is fuller, less spreading and denser in form than 'Polly'.
4. Leaf blades of 'ALO3' are thicker, overall larger, less glossy and have less silver color between veins compared to smaller leaves of 'Polly'.
5. Leaf veins of 'ALO3 are thinner and have narrower silver shadow than 'Polly'.
6. Leaf blades of 'ALO3' are oriented more horizontally whereas leaf blades of 'Polly' are oriented downward
7. The leaf margins of 'ALO3' are green-silver and undulate whereas the leaf margins of 'Polly' are bright sliver and lobed.
8. Leaf petioles of 'ALO3' are light pink with delicate green streaks whereas leaf petioles of 'Polly' are light green to green color with a few very light green streaks.
9. 'ALO3' is more tolerant to disease and stress conditions than 'Polly'.

COMMERCIAL COMPARISON

'ALO3' can be compared to the unpatented species *Alocasia amazonica*. Plants of *Alocasia amazonica* are similar to plants of 'ALO3' in most horticultural characteristics. However 'ALO3' differs from *Alocasia amazonica* in the following characteristics:

1. 'ALO3' is a more vigorous and faster growing plant than *A. amazonica.*
2. 'ALO3' is fuller plant, branches better comparing to *A. amazonica.*
3. Plants of 'ALO3' are shorter, less spread, less open comparing to *A. amazonica.*
4. The form of 'ALO3' is more symmetrical and narrower in diameter compared to *A. amazonica.*
5. The leaf blades of 'ALO3' are thicker, smaller, with less silver color between veins compared to those of *A. amazonica.*
6. Leaf veins of 'ALO3' are surrounded by narrower silver shadow compared to *A. amazonica.*
7. Leaf petioles of 'ALO3' light pink with brown or green streaks, whereas the leaf petioles of *A. amazonica* are light green to green color without distinctive streaks.
8. Leaves of 'ALO3' are oriented more horizontally comparing to downwardly nodding leaves of *A. amazonica.*
9. 'ALO3' is stronger plant, has longer shelf life, it is more tolerant of disease and stress conditions than *A. amazonica.*
10. Leaves of 'ALO3' closely overlap each other whereas the leaves of *A. amazonica* are spreading.

'ALO3' can be compared to the commercial variety *Alocasia* 'ALO2' application Ser. No. 13/986,614. Plants of 'ALO2' are similar to plants of 'ALO3' in most horticultural characteristics. However 'ALO3' differs from 'ALO2' in the following characteristics:

1. Plants of 'ALO3' are taller than plants of 'ALO2'. Typically plants of 'ALO3' grow to 60 cm in height, whereas similar aged plants of 'ALO2' are 45 cm tall.
2. Upper foliage of 'ALO3' has a matte to leathery appearance whereas 'ALO2' has a foliage upper surface which is glossy in appearance.
3. The petiole of 'ALO3' is longer, typically 35 to 45 cm; the petiole of 'ALO2' ranges from 25 to 35 cm.

BRIEF DESCRIPTION OF THE PHOTOGRAPH

The accompanying photograph in FIG. 1 illustrates in full color a typical plant of 'ALO3' grown in a greenhouse in Altha, Fla. This plant is approximately 6 months old, shown in a 6 inch pot.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'ALO3' plants grown in a climate controlled greenhouse in Altha, Fla., USA. Temperatures ranged from 20° C. to 25° C. at night to 25° C. to 32° C. during the day. No artificial light, photoperiodic treatments were given to the plants. Plants were grown in 80% shade, resulting in approximately 800 to 1200 foot candles of light. Measurements and numerical values represent averages of typical plant types.

Botanical classification: *Alocasia* hybrid 'ALO3'.

PROPAGATION

Root description: Thick, fleshy roots. True rhizomes not observed. Roots approximately 0.5 cm thick, colored near RHS White 155A.

PLANT

Growth habit: Rapid, upright. Basal leaves emerge in clumps.
Plant shape: Upright, petioles and leaves slightly arching out. No stems.
Height: Approximately 60 cm to top of foliar plane.
Plant spread: Approximately 45 cm in a 6 inch pot.
Pot size of plant described: 6 inch.
Growth rate: Very rapid, vigorous.
Branching characteristics: No true branching. Leaves emerge direct from base of plant.
Number of clumps of leaves: 4.
Number of leaves per clump: Average 4 to 8.
Number of leaves per plant: Approximately 10 to 30.
Age of plant described: Approximately 6 months.

FOLIAGE

Leaf:

*Arrangement.*—Single leaves emerging basally.

Largest, mature, fully expanded leaf:

*Length* (*excluding petiole*).—Range from 30 to 40 cm.

*Width.*—Range from 15 to 20 cm.

*Shape of blade.*—Sagittate to nearly Hastate, with two very deep lobes that angle upward, rather than flaring outward.

*Aspect.*—Slightly undulating, mainly flat. Puckered.

*Apex.*—Apiculate.

*Base.*—Hastate, with 2 very deep lobes.

*Margin.*—Entire, somewhat undulating.

*Appearance.*—Upper surface matte to almost leathery. Lower surface glossy.

*Texture of top surface.*—Smooth, puckered.

*Texture of bottom surface.*—Smooth, puckered.

*Color.*—Mature foliage upper side: Near RHS Greyed-Green N189A. Mature foliage under side: Near RHS Greyed-Purple 187B.

Venation:

*Type.*—Pinnate.

*Venation coloration upper side.*—Outermost veins near RHS Greyed-Green 191C, secondary veins near RHS Greyed-Green 191B. Center vein, RHS Yellow-Green 147C.

*Venation coloration under side.*—Center vein RHS Yellow-Green 143A, all lateral veins RHS Greyed-Purple 187B.

Petiole:

*Length.*—Approximate range between 35 and 40 cm.

*Width.*—At base: Approximately 1.9 cm. At leaf attachment: Approximately 1.0 cm.

*Color.*—Near RHS Greyed-Red 182B, sparsely covered in short stripes near Brown 200B and moderately covered in short stripes near RHS Greyed-Orange N170D and Yellow-Green 143D. Near leaf attachment, color changes to RHS Yellow-Green 145B, with no stripes approximately 1 cm from attachment point.

*Strength.*—Very strong.

*Texture.*—Glabrous.

*Other.*—Petiole sheath present.

Petiole sheath:

*Length.*—Approximately 5.0 cm to 12 cm.

*Width.*—Approximately 3.0 cm to 4.0 cm.

*Shape.*—Narrow deltoid.

*Color.*—Near RHS Greyed-Red 182D, sparsely covered in short stripes near Brown 200B.

*Texture.*—Glabrous.

Immature foliage:

*Length* (*excluding petiole*).—Range from 17 to 24 cm.

*Width.*—Range from 6 to 9 cm.

*Shape of blade.*—Nearly hastate, with two very deep lobes, angled upward, instead of outward. Youngest leaves less deeply lobed.

*Aspect.*—Slightly undulating, mainly flat. Very slightly puckered.

*Apex.*—Apiculate.

*Base.*—Hastate, with 2 very deep lobes.

*Margin.*—Entire.

*Appearance.*—Young foliage upper surface shiny, lower surface somewhat glossy.

*Texture of top surface.*—Smooth.

*Texture of bottom surface.*—Smooth.

*Color.*—Young foliage upper side: Near RHS Greyed-Green N189A. Young foliage under side: Near RHS Greyed-Purple N186C.

Immature foliage venation:

*Type.*—Pinnate.

*Venation coloration upper side.*—Near RHS Greyed-Green 190B.

*Venation coloration under side.*—Near RHS Green 143A.

INFLORESCENCE

Not observed to date.

OTHER CHARACTERISTICS

Disease resistance: Greater resistance than typical of *Alocasia* to *Myrothecium* and leaf *Phytophthora* has been observed.

Drought tolerance and cold tolerance: The new cultivar is a typical *Alocasia*, cold tolerant to approximately 5 to 7° C. and does not tolerate drought.

Fruit/seed production: Not observed.

What is claimed is:

1. A new and distinct cultivar of *Alocasia* plant named 'ALO3' as herein illustrated and described.

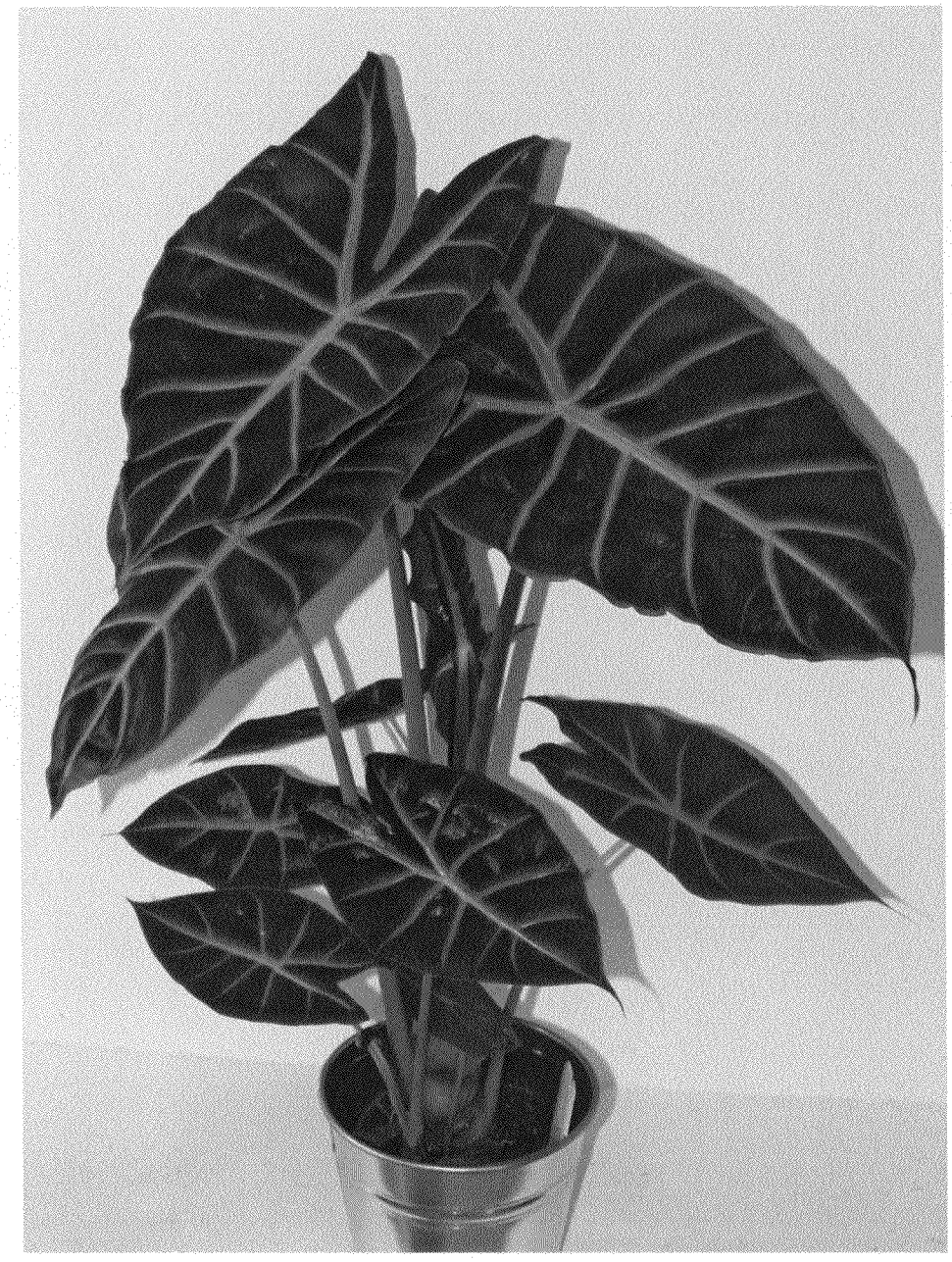

* * * * *